US009121803B2

(12) United States Patent
Ramrattan et al.

(10) Patent No.: US 9,121,803 B2
(45) Date of Patent: Sep. 1, 2015

(54) THERMAL DISTORTION TESTER

(71) Applicant: Western Michigan University Research Foundation, Kalamazoo, MI (US)

(72) Inventors: Sam N. Ramrattan, Kalamazoo, MI (US); Andrew J. Oman, East Jordan, MI (US)

(73) Assignee: Western Michigan University Research Foundation, Kalamazoo, MI (US)

(*) Notice: Subject to any disclaimer, the term of this patent is extended or adjusted under 35 U.S.C. 154(b) by 378 days.

(21) Appl. No.: 13/837,139

(22) Filed: Mar. 15, 2013

(65) Prior Publication Data

US 2013/0243029 A1 Sep. 19, 2013

Related U.S. Application Data

(60) Provisional application No. 61/611,035, filed on Mar. 15, 2012.

(51) Int. Cl.
*G01K 7/00* (2006.01)
*G01N 17/00* (2006.01)
*G01N 25/00* (2006.01)
*G01N 3/56* (2006.01)

(52) U.S. Cl.
CPC ............ *G01N 25/00* (2013.01); *G01N 3/56* (2013.01); *G01N 3/565* (2013.01)

(58) Field of Classification Search
CPC .......... G01K 7/00; G01N 17/00; G01N 25/00
See application file for complete search history.

(56) References Cited

U.S. PATENT DOCUMENTS

| 3,165,924 | A | * | 1/1965 | Wolff | 73/112.01 |
| 3,391,102 | A | * | 7/1968 | Major | 523/138 |
| 3,404,557 | A | * | 10/1968 | Hecht et al. | 73/7 |
| 4,523,475 | A | * | 6/1985 | Bills et al. | 73/781 |
| 4,561,784 | A | * | 12/1985 | Benz et al. | 374/8 |
| 4,759,215 | A | * | 7/1988 | Atchley et al. | 73/167 |
| 5,113,650 | A | * | 5/1992 | Junior et al. | 60/253 |
| 5,419,116 | A | * | 5/1995 | Rast et al. | 60/204 |

(Continued)

FOREIGN PATENT DOCUMENTS

| JP | 60249035 A | 12/1985 |
| JP | 06094588 H | 4/1994 |
| SU | 1195233 | 11/1985 |

OTHER PUBLICATIONS

Rebros et al., Behavior of 3D Printed Sand at Elevated Temperature, American Foundry Society, 2007, pp. 1-8, Schaumburg, IL.

(Continued)

*Primary Examiner* — Lisa Caputo
*Assistant Examiner* — Jamel Williams
(74) *Attorney, Agent, or Firm* — Price Heneveld LLP

(57) ABSTRACT

A thermal distortion tester for testing thermal distortion of a sand specimen, comprising a gimbal to support the sand specimen, an actuator to raise and lower the sand specimen, and a hot surface, wherein the sand specimen is brought into contact with the hot surface at a pre-determined pressure or pressure profile. The temperature of the hot surface is maintained at a pre-determined temperature or temperature profile. The distortion of the sand specimen while applied to the hot surface is directly measured through measurement of the longitudinal movement of the gimbal, and radial distortion is measured by a micrometer camera. The temperature gradient of the sand specimen is also measured throughout the duration of the test. A method of using the same is also described herein.

20 Claims, 3 Drawing Sheets

(56) References Cited

U.S. PATENT DOCUMENTS

| | | | |
|---|---|---|---|
| 5,419,119 A * | 5/1995 | Obney | 60/253 |
| 6,054,521 A * | 4/2000 | Nelson et al. | 524/405 |
| 7,628,534 B2 * | 12/2009 | Deoclezian et al. | 374/7 |
| 2011/0220316 A1 | 9/2011 | Fuqua et al. | |

OTHER PUBLICATIONS

Rodriguez et al., Development of Apparatus and Protocol for Testing of Sand at High Temperatures in the Foundry, American Society for Engineering Education, 2007, 9 pages.

Ramrattan et al., Comparing Casting Evaluation to Thermal Distortion Testing for Various Chemically Bonded Sand Systems Using Image Analysis, American Foundry Society, 2011, pp. 1-10, Schaumburg, IL.

Ramrattan et al., Wet to Dry—Refractory Coating Control for Precision PUCB Sands, International Journal of Metalcasting, 2011, 20 pages, vol. 5, Issue 2, American Foundry Society, Inc.

International Search Report and Written Opinion, Sep. 5, 2013, from International Application No. PCT/US2013/041161, 6 pages.

* cited by examiner

THERMAL DISTORTION TESTER

CROSS REFERENCE TO RELATED APPLICATIONS

This application claims priority under 35 U.S.C. §119(e) to U.S. Provisional Patent Application No. 61/611,035, filed Mar. 15, 2012, entitled "THERMAL DISTORTION TESTER", which is herein incorporated by reference in its entirety.

BACKGROUND OF THE INVENTION

Bonded sand cores and molds, comprising sand and binder systems, are an important part of metal casting technology. Binder materials for use with sand cores and molds may include chemical binders or clay binders. The behavior of the sand and binder system when placed in contact with molten metal is important for determining the quality of metal parts cast using the bonded sand cores and molds. Additionally, every year, foundry industry groups and companies spend millions of dollars on refractory coatings for bonded sand cores and molds. Refractory coatings have been used to aid in surface finish improvements, and to reduce thermal expansion defects such as veining and un-bonded sand defects such as erosion.

Directional heating of bonded sand cores and molds generates anisotropic thermal gradients in the bonded sand composite material. When the shaped sand composite comes into contact with molten metal, the heat transferred from the molten metal to the sand composite causes thermo-chemical reactions that result in dimensional changes in the sand composite and thus the shape and size of the cores and molds. At any given temperature, these dimensional changes or thermal distortions are attributable to simultaneous changes in both the sand and the binder material.

In bonded sand systems, thermo-chemical reactions generally include the release of volatile materials, possible core strengthening reactions from secondary curing, and core weakening from pyrolysis. It is important to understand and distinguish between thermo-mechanical distortions caused by changes in the binder and thermo-mechanical distortions caused by changes in the sand base. It is also important to understand the likely behavior of the core or mold when molten metal is poured over the mold.

SUMMARY OF THE INVENTION

One aspect of the present invention includes a thermal distortion tester, including a gimbal which has a top surface that is adapted to support a sand specimen. A hot surface is disposed above the gimbal. An actuator is operatively connected to the gimbal to raise the gimbal until the sand specimen supportable thereon contacts the hot surface. The actuator is adapted to apply a variable upwardly directed force to press the sand specimen against the hot surface.

Another aspect of the invention includes a method of testing thermal distortion of a sand specimen. The method includes the steps of supporting a sand specimen, and bringing the sand specimen into contact with a hot surface, wherein the hot surface is set to a pre-determined temperature profile. A pre-determined load is applied to the sand specimen, to press it against the hot surface. The distortion of the sand specimen is measured while the pre-determined load is applied thereto.

Another aspect of the invention includes a method of testing thermal distortion of a sand specimen, including the steps of supporting a sand specimen and bringing the sand specimen into contact with a hot surface. A pre-determined load is applied to the sand specimen, to press it against the hot surface. The load applied to the sand specimen is varied during the test.

These and other features, advantages, and objects of the present invention will be further understood and appreciated by those skilled in the art by reference to the following specification, claims, and appended drawings.

DETAILED DESCRIPTION

A thermal distortion tester ("TDT") 10 as described herein can be used to study the strength and distortion of bonded sand, with or without the refractory coatings, and to predict the behavior of bonded sand and optional refractory coating when it is incorporated into a sand core or mold. The TDT 10 described herein is suitable for measuring the thermo-mechanical behavior of refractory coated or uncoated sand systems using a disc-shaped specimen 12 of the sand system. The TDT described herein is also suitable for on-site testing where sand cores or molds are used, because it is robustly designed and portable.

Figure 1:
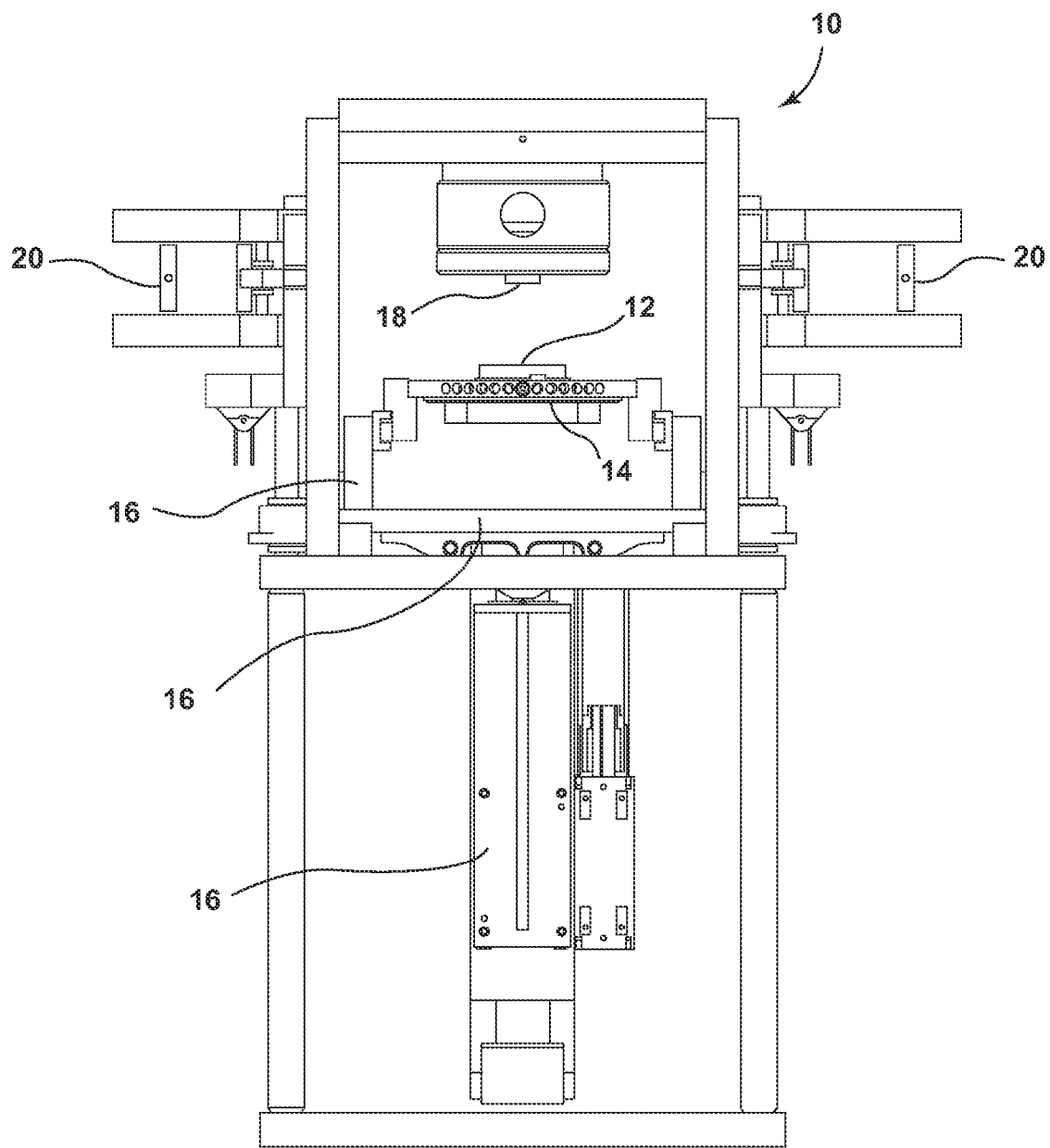
FIG. 1 is a plan view of one embodiment of a thermal distortion tester.

One embodiment of the TDT 10 as shown in FIG. 1 comprises a pivoting holder (gimbal) 14, an actuator 16 operatively connected to gimbal 14 to raise and lower gimbal 14, and a hot surface 18 located above gimbal 14, and preferably centered above gimbal 14. A micrometer camera 20 is positioned to observe the radial expansion of sand specimen 12 during the test.

Figure 2:
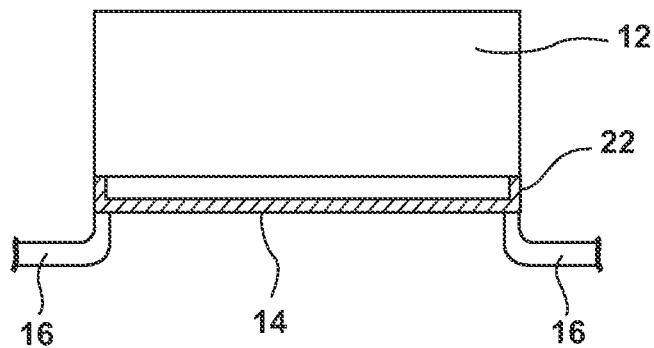
FIG. 2 is an enlarged cross sectional view of one embodiment of the sand specimen as placed in the thermal distortion tester.
Figure 3:
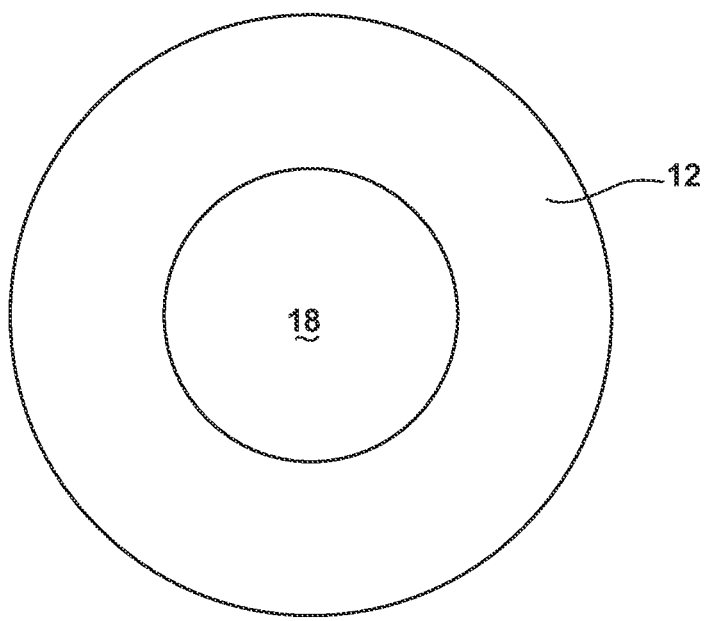
FIG. 3 is a top view of the hot surface and sand specimen disc in position for carrying out a thermal distortion test.

Gimbal 14 is adapted to hold various thicknesses of the sand specimens 12. As shown in FIG. 2, gimbal 14 has a raised edge 22 around its circumference which simple-supports sand specimen 12 about its circumference when specimen 12 is placed thereon. The thickness of raised edge 22 is preferably about 1 mm, such that pressure is applied to the outside 1 mm of sand specimen 12. Sand specimens 12, and gimbal 14, preferably measure about 5.00 cm in diameter. Sand specimen 12 preferably has a thickness of from about 3 mm to about 0.8 cm thick. The diameter and thickness of sand specimen 12 can be varied, though when measurements relating to different sand and binder systems are being compared, such comparison can benefit from the use of a standardized diameter and thickness of sand specimen 12. Hot surface 18 preferably has a diameter which is smaller than the diameter of the sand specimen 12, as shown in FIG. 3. Preferably, the diameter of hot surface 18 is about 2.00 cm.

Actuator 16 is operatively connected to gimbal 14, to raise and lower gimbal 14, such that the sand specimen 12 placed thereon comes into contact with hot surface 18. The sand specimen 12 is preferably brought into contact with the entire hot surface 18. The pivoting action of gimbal 14 ensures that when sand specimen 12 is raised to contact hot surface 18, uniform, symmetrical pressure is applied across the top surface of sand specimen 12. The variable positioning of actuator 16, to raise sand specimen 12 into contact with hot surface 18 allows operators to test varying thicknesses of sand specimens 12 to simulate various mold thicknesses. During a given test, actuator 16 raises sand specimen 12 to press against hot surface 18, and then actuator 16 maintains a predetermined load against sand specimen 12 to press sand specimen 12 against hot surface 18. The predetermined load is preferably chosen by the operator to represent the force of molten metal pressing against the wall of a mold or core in the operation for which the sand specimen 12 composition is being tested. Different loading pressures simulate different metallostatic pressures that might be encountered by a mold or core during casting. Additionally, actuator 16 can apply varying pressure to sand specimen 12 over time, to simulate pressure changes that would be experienced by a mold or core during and after the pouring of molten metal into the mold. The changing pressure can be used to simulate changing head pressure including during casting, including simulation of large mold castings.

In addition to raising and lowering gimbal 14, actuator 16 simultaneously measures longitudinal distortion (in the direction perpendicular to hot surface 18) and tracks the pressure on sand specimen 12. Longitudinal distortion is directly measured by measuring movement of actuator 16 required to maintain the pre-determined load profile. Alternatively, actuator 16 can be set at a fixed position, and can measure varying loads created by sand specimen 12.

The temperature of hot surface 18 is controlled to maintain a constant temperature or to follow a pre-determined temperature profile throughout the test to simulate operating conditions for a mold or core comprising the same type of sand composition as sand specimen 12. An electronic resistance-based system can be used to control the temperature of hot surface 18. An induction furnace as a source of heat for hot surface 18 is preferred over an electronic resistance-based system, due to its repeatability and consistency. One method of controlling the temperature of hot surface 12 is through use of a K-type thermocouple located at hot surface 18, connected to a controller device or computer. TDT 10 preferably has a hot surface 18 capable of maintaining various temperature settings, so that TDT 10 can be used to simulate the effects of various types of alloys, such as an interfacial temperature between molten aluminum and a sand mold of about 700° C. and an interfacial temperature between molten cast iron and a sand mold of about 1000° C.

The duration of the thermal distortion test can be varied, for example, to simulate the conditions expected to be encountered when a mold or core having the same composition as sand specimen 12 is used in foundry operations. Preferably, test time is sufficient to achieve steady state in terms of the temperature of the interface between sand specimen 12 and hot surface 18, to apply a consistent load-temperature to specimen 12 and for reliable data collection to take place. In one embodiment, the thermal distortion testing is carried out at a specified load for about 3 minutes.

An IR sensor 24 may optionally be provided to measure the temperature gradient formed longitudinally in the sand specimen 12 upon heating via contact with hot surface 18 during the test. The IR sensor 24 measures the temperature gradient throughout the entire length of the test, and can optionally provide continuous monitoring of the temperature gradient. Measuring temperature gradients in sand specimen 12 permits measurement of heat dissipation properties and permits correlation of these properties over time with longitudinal and radial expansion and distortion.

The TDT preferably includes an electronic interface with a computer, a computer, and a data acquisition system to control and monitor the TDT and to plot graphs representing the pressure, hot surface temperature, temperature gradients, time and sand specimen distortions, such as radial and longitudinal expansion and plastic distortion, collected by TDT 10 during the test. Such system preferably automatically logs and plots at least one of the pressure, temperature, temperature gradient, and distortion parameters, versus time for each test that is run.

Figure 4:
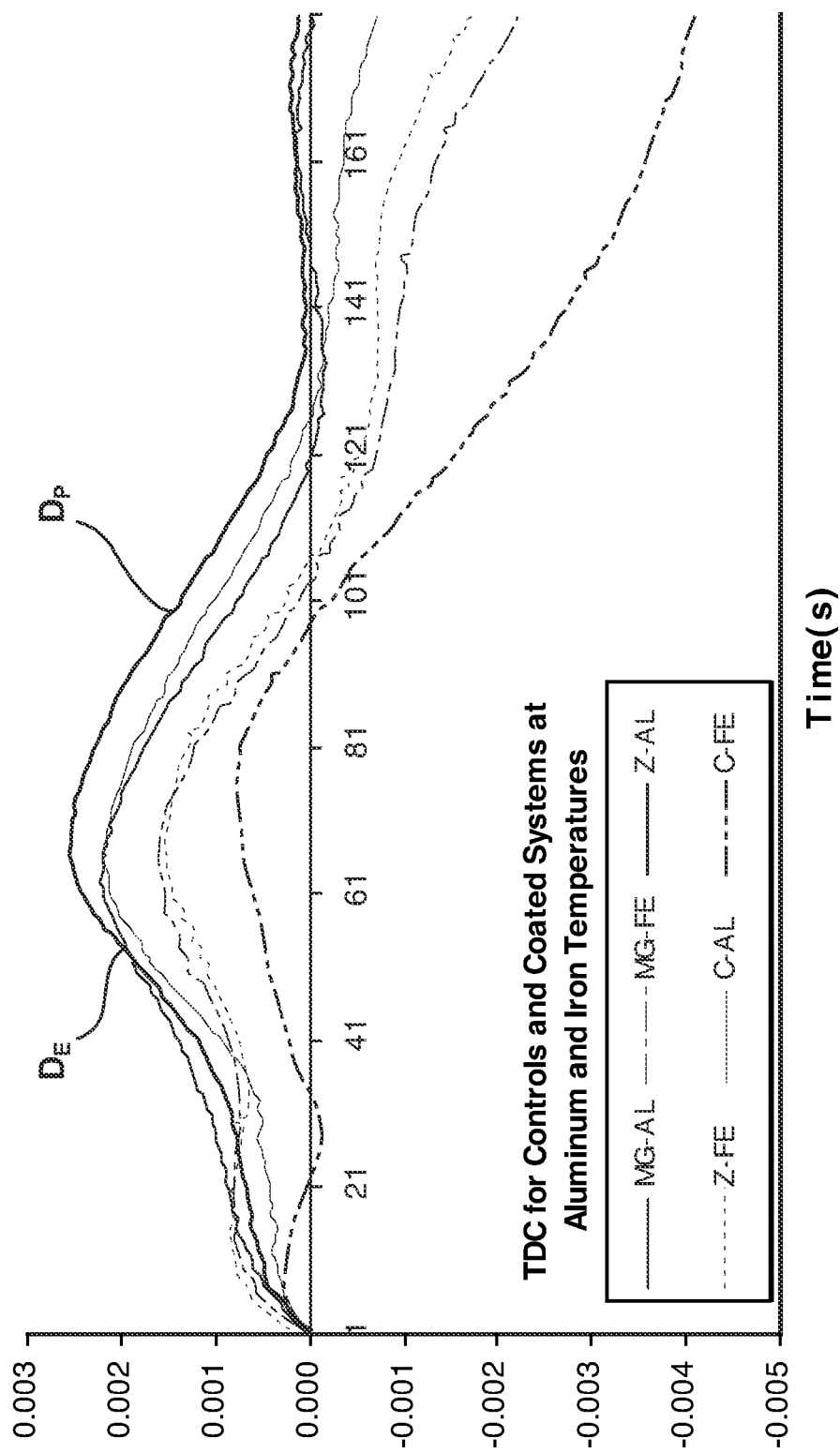
FIG. 4 is a plot of distortion versus time data collected in a thermal distortion test.

To measure and plot distortion, any downward movement of gimbal 14 is measured or recorded as expansion ($D_E$) of sand specimen 12, and any upward movement of gimbal 14 is measured or recorded as plastic distortion ($D_P$) of sand specimen 12. A lever system may be implemented to accurately measure distortion of sand specimen 12. As an example, when plotted, expansion (downward movement of gimbal 14) appears as an upward trend when plotted on a distortion versus time curve, and plastic distortion (upward movement of gimbal 14) appears as a downward trend when plotted on a distortion versus time curve. (FIG. 4.) For longitudinal axis distortion, it is possible to differentiate between expansion and plastic distortion based on the thermal distortion curve. The total distortion ($D_T$) is the sum of expansion ($D_E$) and plastic distortion ($D_P$), or $$D_T = \Sigma v \mu D_E + \Sigma v \mu D_P.$$

Radial expansion, pressure change, temperature changes, temperature gradient changes or profile changes with time may be plotted individually or concomitantly with the distortion versus time curve.

After completion of the test procedure and thermal exposure of sand specimen 12, sand specimen 12 is often intact, thereby allowing determination of additional valuable information from sand specimen 12, in addition to distortion properties. Such additional determinations or further evaluations may include a visual analysis of sand specimen 12 for cracks (which in an operational metal-casting process, could result in veining of the molded parts), measurement of final sand specimen weight (which provides information relating to, for example, pyrolysis of binder bridges and the amount of loose unbounded sand generated), and measurement of the retained strength of sand specimen 12.

Thermal distortion testing of sand can be undertaken in addition to various other tests to predict the behavior of a mold or core made using the same composition as sand specimen 12. For example, sand specimens can be prepared and then subjected to disc transverse strength testing, scratch hardness testing, erosion testing, jolt testing, and thermal distortion testing to obtain information about the likely behavior of a mold or core made using the sand specimen 12 composition.

In one example, disc sand specimens 12 were prepared using silica sand (Illinois AFS/gfn 50, rounded and neutral pH) and binders, using a laboratory sand mixer and a jig and fixture for 5-cm diameter by 0.80-cm thick disc-shaped specimen 12. The binder to sand ratio was one which was specified for testing, typically based on a percentage of weight. The sand and binder were mixed for two minutes. Test sand specimens 12 were prepared by blowing the sand-binder mixture at 552 KPa air pressure from a core-shooter into the disc-shaped specimen jig and fixtures. The disc-shaped specimen and jig have removable plates, so that sand specimens 12 were easily removed without deformation, and were placed on a flat surface to complete the hardening process.

A disc sand specimen 12 was then transverse strength tested using a Tinius Olsen testing machine equipped with disc-shaped specimen holder and blade for performing the test. Sand specimen 12 was fitted into a specimen holder on the testing machine and supported on its ends. Sand specimen 12 was then subjected to a transverse force by applying the load with a 3-mm thick blade across its diameter, with loading at a constant load rate of 0.25 cm/min. A load-cell electronically sensed and responded to sand specimen 12 failure. The maximum load at failure was measured and digitally displayed by the testing device.

Disc sand specimen 12 was also tested using a scratch hardness tester, according to standard AFS scratch hardness test 318-87-S.

A disc sand specimen 12 was then tested using thermal distortion tester 10, while this set of tests should not be considered limiting. Hot surface 18 was heated to 760° C. to simulate use of molten aluminum. Sand specimen 12 was inserted into gimbal 14, and lowered until a direct symmetrical contact was made with hot surface 18, having a 2.00-cm diameter. Sand specimen 12 was held in contact with hot surface 18 under a predetermined load of 5 Newtons (N) to simulate hydrostatic force pressing against a core or mold, applied to the circumference of specimen 12 by edge 22 of gimbal 14. The data acquisition system of TDT 10 measures, records and plots distortion, radial expansion and thermal gradient changes versus time.

Thus, an embodiment of the invention is directed to a thermal distortion tester 10, comprising a gimbal 14 to support a sand specimen 12; a hot surface 18, capable of providing a pre-determined temperature or temperature profile; an actuator 16, wherein the actuator 16 is operatively connected to the gimbal 14 to raise the gimbal 14 such that the sand specimen 12 supported thereon comes into contact with the hot surface 18, and wherein the actuator 16 is capable of applying a pre-determined load or load profile to the sand specimen 12. Additional embodiments include the capability to apply a pre-determined temperature or temperature profile using the hot plate, temperature sensors to measure the temperature gradient of the sand specimen 12 during the test, sample distortion measurement sensors, a control and data collection device, and a method of testing the thermal distortion of a sand specimen 12.

The thermal distortion tester 10 described herein provides advantages for use in foundry operations, as the variable load and temperatures applied to the sand specimen 12, as well as the ability to test sand specimens 12 of varying thickness, allow the test to more accurately predict how a mold or core made from the same materials as the sand specimen 12 will perform under real world conditions, including filling of a large mold and the use of the mold for various materials with differing melt points. Continuous direct measurement of the distortion of the sand specimen 12 and the temperature gradient experienced by the sand specimen 12 provide additional useful data in predicting the performance of a mold or core. The TDT 10 is also portable and robust, allowing it to be used on-site in foundry locations.

In the foregoing specification, specific embodiments of the present invention have been described. However, one of ordinary skill in the art appreciates that various modifications and changes can be made without departing from the scope of the present invention as set forth in the claims below. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

The invention claimed is:

1. A thermal distortion tester, comprising:
   a gimbal which has a top surface that is adapted to support a sand specimen;
   a hot surface which is disposed above the gimbal; and
   an actuator, wherein the actuator is operatively connected to the gimbal to raise the gimbal until the sand specimen supportable thereon contacts the hot surface, and wherein the actuator is adapted to apply a variable upwardly directed force to press the sand specimen against the hot surface.

2. The thermal distortion tester of claim 1, wherein the variable upwardly directed force is capable of being varied over the duration of a test.

3. The thermal distortion tester of claim 1, wherein the hot surface is adapted to have a temperature which is variable during a single test.

4. The thermal distortion tester of claim 1, wherein the actuator is further adapted to measure longitudinal distortion of the sand specimen while the actuator maintains a constant pressure of the sand specimen against the hot surface.

5. The thermal distortion tester of claim 1, wherein the actuator is further adapted to maintain a fixed position during a test and measure the varying load created by the sand specimen while it is in contact with the hot surface.

6. The thermal distortion tester of claim 1, further comprising a raised edge around a circumference of the gimbal which is adapted to support the sand specimen about a circumference of the sand specimen.

7. The thermal distortion tester of claim 6, wherein the hot surface and the top surface are generally round, and wherein the diameter of the top surface is greater than the diameter of the hot surface.

8. The thermal distortion tester of claim 7, wherein the gimbal is pivotally coupled to the thermal distortion tester.

9. The thermal distortion tester of claim 1, further comprising:
   an IR sensor adapted to continuously measure a temperature gradient formed in the sand specimen upon contact with the hot surface.

10. A method of testing thermal distortion of a sand specimen, comprising the steps of:
    supporting a sand specimen;
    bringing the sand specimen into contact with a hot surface, wherein the hot surface is set to a pre-determined temperature profile;
    applying a pre-determined load to the sand specimen, to press it against the hot surface; and
    measuring the distortion of the sand specimen while the pre-determined load is applied thereto.

11. The method of testing the thermal distortion of a sand specimen of claim 10, wherein the longitudinal distortion of the sand specimen is directly measured by an actuator.

12. The method of testing the thermal distortion of a sand specimen of claim 11, wherein radial distortion of the sand specimen is measured optically.

13. The method of testing the thermal distortion of a sand specimen of claim 10, wherein the pre-determined temperature profile simulates the temperature of a molten metal during casting.

14. The method of testing the thermal distortion of a sand specimen of claim 10, wherein the pre-determined load simulates the pressure of a molten metal against a mold during casting.

15. A method of testing thermal distortion of a sand specimen, comprising the steps of:
supporting a sand specimen;
bringing the sand specimen into contact with a hot surface;
applying a pre-determined load to the sand specimen, to press it against the hot surface; and
varying the load applied to the sand specimen during the test.

16. The method of testing thermal distortion of a sand specimen of claim 15, wherein the load is selected to simulate the pressure of molten metal during casting.

17. The method of testing the thermal distortion of a sand specimen of claim 15, wherein the hot surface is maintained at a pre-determined temperature profile, and wherein the pre-determined temperature profile simulates the temperature of a molten metal during casting.

18. The method of testing the thermal distortion of a sand specimen of claim 15, further comprising the step of:
measuring longitudinal distortion in a direction perpendicular to the hot surface while the pre-determined load is applied to the sand specimen.

19. The method of testing the thermal distortion of a sand specimen of claim 15, further comprising the step of measuring a temperature gradient formed longitudinally in the sand specimen by the contact with the hot surface.

20. The method of testing the thermal distortion of a sand specimen of claim 15, further comprising the steps of:
measuring the distortion of the sand specimen to obtain a first measurement;
measuring elapsed time of a test to obtain a second measurement; and
plotting a graph of the first measurement with respect to the second measurement.

* * * * *